United States Patent [19]
Kumar

[11] Patent Number: 5,429,774
[45] Date of Patent: Jul. 4, 1995

[54] BENZOPYRAN COMPOUNDS

[75] Inventor: Anil Kumar, Pittsburgh, Pa.

[73] Assignee: Transitions Optical, Inc., Pinellas Park, Fla.

[21] Appl. No.: 220,344

[22] Filed: Mar. 30, 1994

Related U.S. Application Data

[63] Continuation-in-part of Ser. No. 201,948, Feb. 25, 1994, which is a continuation-in-part of Ser. No. 30,932, Mar. 12, 1993.

[51] Int. Cl.$^6$ .................. G02B 5/23; C07D 311/78; C07D 311/92; C07D 333/50
[52] U.S. Cl. ........................ 252/586; 549/42; 549/383; 549/389; 549/457
[58] Field of Search ............... 549/42, 382, 383, 457, 549/389; 252/586

[56] References Cited

U.S. PATENT DOCUMENTS

| | | | |
|---|---|---|---|
| 2,894,003 | 7/1959 | Long et al. | 260/346.2 |
| 2,900,396 | 8/1959 | Harrison | 260/346.1 |
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 4,215,010 | 7/1980 | Hovey et al. | 252/300 |
| 4,342,668 | 8/1982 | Hovey et al. | 252/586 |
| 4,637,698 | 1/1987 | Kwak et al. | 351/163 |
| 4,720,356 | 1/1988 | Chu | 252/586 |
| 4,816,584 | 3/1988 | Kwak et al. | 544/71 |
| 4,818,096 | 4/1988 | Heller et al. | 351/163 |
| 4,826,977 | 5/1989 | Heller et al. | 544/70 |
| 4,931,221 | 6/1990 | Heller | 252/586 |
| 4,980,089 | 12/1990 | Heller | 252/586 |
| 4,990,287 | 2/1991 | Bennion et al. | 252/586 |
| 5,066,818 | 11/1991 | Van Gemert | 549/389 |
| 5,200,116 | 4/1993 | Heller | 252/586 |
| 5,238,981 | 8/1993 | Knowles | 252/586 |
| 5,244,602 | 9/1993 | Van Gemert | 252/589 |
| 5,274,132 | 12/1993 | Van Gemert | 549/389 |

FOREIGN PATENT DOCUMENTS 816719 8/1937 France .

OTHER PUBLICATIONS

Friedel-Crafts and Related Reactions, George A. Olah, Interscience Publishers, vol. 3, Chap. XXXI, pp. 1–8, 1964.
"Regioselective Friedel-Crafts Acylation of 1,2,3,4-Tetrahydroquinoline and Related Nitrogen Heterocycles", Ishihara, Yugi et al, J. Chem. Soc., Perkin Trans. 1, pp. 3401–3406, 1992.
Heterocyclic Compounds, R. C. Elderfield, 1951, vol. 2, Chapters 3 and 5, pp. 123–144, pp. 164–172.
The Chemistry of Heterocyclic Compounds, H. D. Hartough et al, 1954, vol. 7, Chapter IV, pp. 225–282.
Advances in Heterocyclic Chemistry, A. R. Katritzky et al, 1974, vol. 16, Chapter V.
Akermark et al, Acta Chemica Scandinavica, vol. 13, 1959, pp. 1855–1862.
S. Granowitz et al, Acta Pharm. Suec., vol. 15, 1978, pp. 337–360.
J.A.C.S. vol. 61, Apr. 1939, pp. 951–956; Dibenzofuran. IX Metalation of Some Derivatives.
J.A.C.S. vol. 87(2), 1965, pp. 213–217; The Electron Spin Resonance Spectra of the Dibenzothiophene Radical Anion and its Isologs and the Electronic Structure of Conjugated Sulfur-Containing Heterocycles.
J.A.C.S. vol. 62, Mar. 1940, pp. 667–669. DiBenzofuran. XVIII. Isomeric Metalation Products of Some Phenols and their Methyl Ethers.

*Primary Examiner*—Philip Tucker
*Attorney, Agent, or Firm*—Frank P. Mallak; Irwin M. Stein

[57] ABSTRACT

Described are novel reversible photochromic benzopyran compounds, examples of which are compounds having the 2,3 position of a benzofurano or benzothieno group fused to the f, g, or h side of the benzopyran, or a benzo group fused to the f side of the benzopyran, and (i) a substituted or unsubstituted phenyl and (ii) a substituted or unsubstituted benzothienyl or benzofuranyl group attached (via the 2 or 3 position of the group) at the 2 position of the pyran ring. Also described are organic host materials that contain or that are coated with such compounds. Articles such as ophthalmic lenses or other plastic transparencies that incorporate the novel benzopyran compounds or combinations thereof with complementary photochromic compounds, e.g., spiro (indoline) type compounds, are also described.

22 Claims, No Drawings

BENZOPYRAN COMPOUNDS

This application is a continuation in part of application Ser. No. 08/201,948 filed Feb. 25, 1994 which is a continuation in part of abandoned application Ser. No. 08/030,932, filed Mar. 12, 1993.

DESCRIPTION OF THE INVENTION

The present invention relates to certain novel benzopyran compounds. More particularly, this invention relates to novel photochromic benzopyran compounds and to compositions and articles containing such novel benzopyran compounds. When exposed to light radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about $-30°$ C. Irradiation of the compounds with visible light or upon raising the temperature to above about $0°$ C. is reported to reverse the coloration to a colorless state.

The present invention relates to novel benzopyran compounds which exhibit color changes from colorless to colors ranging from yellow to red/purple. These compounds are substituted at the 2 position of the pyran ring with (i) a substituted or unsubstituted phenyl and (ii) a substituted or unsubstituted benzothienyl or benzofuranyl group, and have a benzo group, or a substituted or unsubstituted benzothieno or benzofurano group fused to the benzo portion of the benzopyran. The benzothienyl or benzofuranyl group is attached to the pyran ring at their 2 or 3 positions. The benzothieno or benzofurano group is fused to the f, g, or h side of the benzopyran at their 2,3-positions; and the benzo group is fused to the f side of the benzopyran.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

Photochromic compounds useful in optical applications, such as conventional ophthalmic lenses, are those which possess (a) a high quantum efficiency for coloring in the near ultraviolet, (b) a low quantum yield for bleaching with white light, and (c) a relatively fast thermal fade at ambient temperature but not so rapid a thermal fade rate that the combination of white light bleaching and thermal fade prevent coloring by the ultraviolet component of strong sunlight. In addition, the aforesaid properties are desirably retained in conventional rigid synthetic plastic materials customarily used for vision correcting ophthalmic and plano lenses when such materials have applied to or incorporated therein such photochromic compounds.

In accordance with the present invention, it has now been discovered that certain novel benzopyran compounds which exhibit color changes from colorless to colors ranging from yellow to red/purple may be prepared. These compounds may be described as benzopyrans having the 2,3 positions of a benzofurano or benzothieno group fused to the f, g, or h side or a benzo group fused to the f side of the benzopyran, and (i) a substituted or unsubstituted phenyl and (ii) a substituted or unsubstituted benzothienyl or benzofuranyl group attached (via the 2 or 3 position of the group) at the 2 position of the pyran ring. The benzopyrans of the present invention may be represented by the following graphic formula:

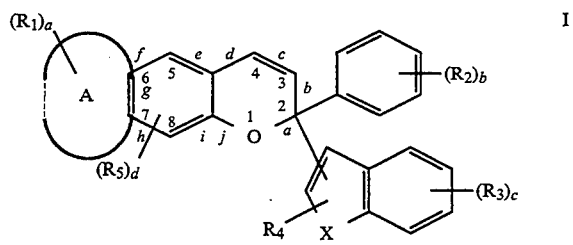

In graphic formula I, A may be selected from the group consisting of benzothieno, benzofurano, and benzo. The benzothieno or benzofurano group A may be represented by the following graphic formula:

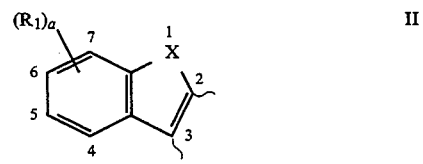

When A is a benzothieno or benzofurano group represented by graphic formula II, isomers may exist depending on the orientation of attachment as demonstrated in graphic formulae I C and I E. In graphic formulae I and II, X may be oxygen or sulfur. Each $R_1$ may be $C_1$-$C_5$ alkyl, e.g., methyl, ethyl, propyl, butyl and pentyl, $C_5$-$C_7$ cycloalkyl, e.g., cyclopentyl, cyclohexyl, and cycloheptyl, $C_1$-$C_5$ alkyl substituted $C_5$-$C_7$ cycloalkyl, $C_1$-$C_5$ alkylcarbonyl, $C_1$-$C_5$ alkoxycarbonyl, halo($C_1$-$C_5$)alkylcarbonyl, which includes mono-, di-, or tri-halo substituents, $C_1$-$C_5$ monoalkylaminocarbonyl, formyl, halogen, R(R')N—, or the group, —O—L, wherein R is $C_1$-$C_3$ alkyl, R' is hydrogen or $C_1$-$C_3$ alkyl, L is hydrogen, $C_1$-$C_5$ alkyl, phenyl($C_1$-$C_3$)alkyl, $C_1$-$C_5$ alkylcarbonyl, halo($C_1$-$C_5$)alkylcarbonyl, $C_1$-$C_5$ monoalkylaminocarbonyl, acrylyl, methacrylyl, acetonyl, pyridyl, or substituted or unsubstituted arylcarbonyl, said aryl of the arylcarbonyl group being phenyl or naphthyl, said aryl substituents being $C_1$-$C_5$ alkyl, $C_1$-$C_5$ alkoxy, halogen, $C_5$-$C_7$ cycloalkyl, or $C_1$-$C_5$ alkyl substituted $C_5$-$C_7$ cycloalkyl, and said halogen (or halo) groups being chloro, fluoro, or bromo. More preferably, $R_1$ is $C_1$-$C_3$ alkyl, $C_5$-$C_6$ cycloalkyl, $C_1$-$C_3$ alkylcarbonyl, $C_1$-$C_3$ alkoxycarbonyl, halo($C_1$-$C_2$)alkylcarbonyl, $C_1$-$C_3$ alkylaminocarbonyl, formyl, chloro, fluoro, R(R')N—, or the group, —O—L, wherein R is $C_1$-$C_2$ alkyl, R' is hydrogen or $C_1$-$C_2$ alkyl, L is $C_1$-$C_3$ alkyl, phenyl($C_1$-$C_2$)alkyl, $C_1$-$C_3$ alkylcarbonyl, $C_1$-$C_3$ alkoxycarbonyl, halo($C_1$-$C_2$)alkylcarbonyl, $C_1$-$C_3$ monoalkylaminocarbonyl, acrylyl, or methacrylyl, and said halo group being chloro or fluoro. Most preferably, $R_1$ is formyl, methyl, methoxycarbonyl, methylaminocarbonyl, or methoxy.

Each $R_2$ in graphic formula I may be $C_1$-$C_5$ alkyl, $C_5$-$C_7$ cycloalkyl, halogen, R(R')N—, or the group, —O—L', wherein the halogen, R and R' are as defined hereinbefore, and said L' is hydrogen, $C_1$-$C_5$ alkyl, phenyl($C_1$-$C_3$)alkyl, acrylyl, or methacrylyl. More preferably, each $R_2$ is $C_1$-$C_3$ alkyl, $C_5$-$C_6$ cycloalkyl, fluoro, R(R')N—, or the group, —O—L', wherein R is $C_1$-$C_2$ alkyl, R' is hydrogen or $C_1$-$C_2$ alkyl, and L' is $C_1$-$C_3$ alkyl, phenyl($C_1$-$C_2$)alkyl, acrylyl, or methacrylyl. Most preferably, each $R_2$ is methyl, methoxy, or fluoro.

Each $R_3$ in graphic formula I may be $C_1$-$C_5$ alkyl or $C_1$-$C_5$ alkoxy. More preferably, each $R_3$ may be $C_1$-$C_3$ alkyl or $C_1$-$C_3$ alkoxy. Most preferably, each $R_3$ is methyl or methoxy. $R_4$ in graphic formula I may be hydrogen or $C_1$-$C_5$ alkyl. More preferably, $R_4$ is hydrogen or $C_1$-$C_3$ alkyl. Most preferably, $R_4$ is methyl. Each $R_5$ in graphic formula I may be $C_1$-$C_5$ alkyl, $C_5$-$C_7$ cycloalkyl, $C_1$-$C_5$ alkylcarbonyl, $C_1$-$C_5$ alkoxycarbonyl, halo($C_1$-$C_5$)alkylcarbonyl, $C_1$-$C_5$ monoalkylaminocarbonyl, formyl, halogen, cyano, R(R')N—, or the group, —O—L, wherein the halogen (halo), R, R', and L are as defined hereinbefore. More preferably, $R_5$ is formyl, $C_1$-$C_3$ alkyl, $C_5$-$C_6$ cycloalkyl, $C_1$-$C_3$ alkylcarbonyl, $C_1$-$C_3$ alkoxycarbonyl, halo($C_1$-$C_3$)alkylcarbonyl, $C_1$-$C_3$ monoalkylaminocarbonyl, fluoro, R(R')N—, or the group, —O—L. Most preferably, $R_5$ is formyl, methyl, methoxycarbonyl, methylaminocarbonyl, or methoxy. The letters a, b, c, and d in graphic formula I are each the integers 0, 1, or 2, provided that when A is benzo, a and d are each 0. More preferably, a, b, c, and d are each the integers 0 or 1.

Graphic formulae I A through I F include some of the potential structures of the benzopyrans of the present invention. In each graphic formula X may be oxygen or sulfur.

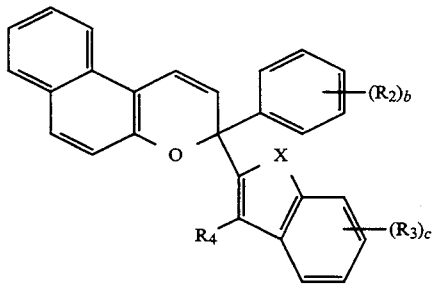

I A

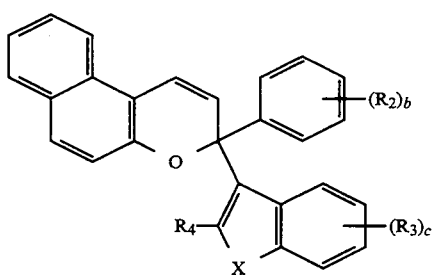

I B

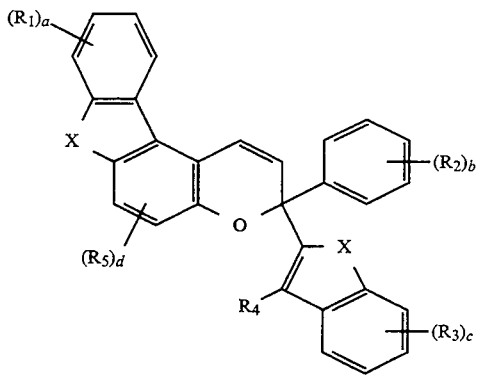

I C

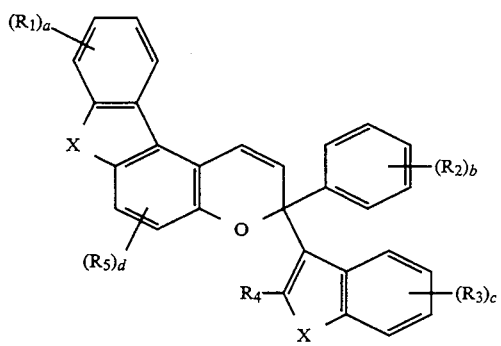

I D

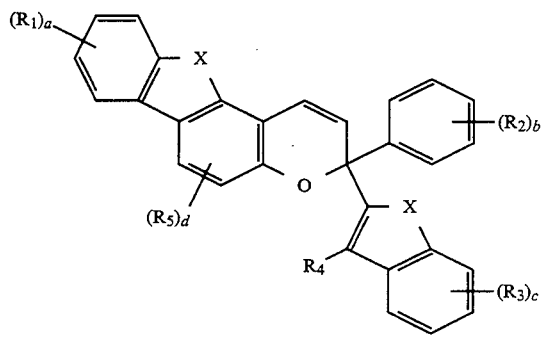

I E

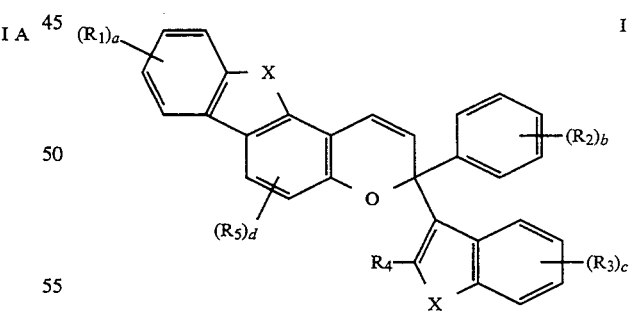

I F

Compounds represented by graphic formula I, which also include graphic formulae I A, I B, I C, I D, I E, I F, I G, I H, and I I, may be prepared by a coupling reaction of an appropriately substituted or unsubstituted propargyl alcohol with 2-naphthol or an appropriately substituted or unsubstituted hydroxydibenzothiophene or hydroxydibenzofuran as described in Reaction C. The propargyl alcohol may be prepared as described in Reaction B using the benzoyl derivative at the 2 position of the benzothiophene or benzofuran prepared in Reaction A. The benzoyl derivative at the 3 position of the benzothiophene or benzofuran may be prepared by Friedel-Crafts methods. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

In Reaction A, the benzofuran or benzothiophene represented by graphic formula III, having $R_3$ as a $C_1$-$C_5$ alkyl, is dissolved in a solvent, such as tetrahydrofuran, and reacted with n-butyl lithium to form the lithium derivative represented by graphic formula IV. This material is reacted with a substituted or unsubstituted benzonitrile, represented by $(R_2)_b PhCN$, followed by hydrolysis to produce the desired ketone represented by graphic formula V.

REACTION A

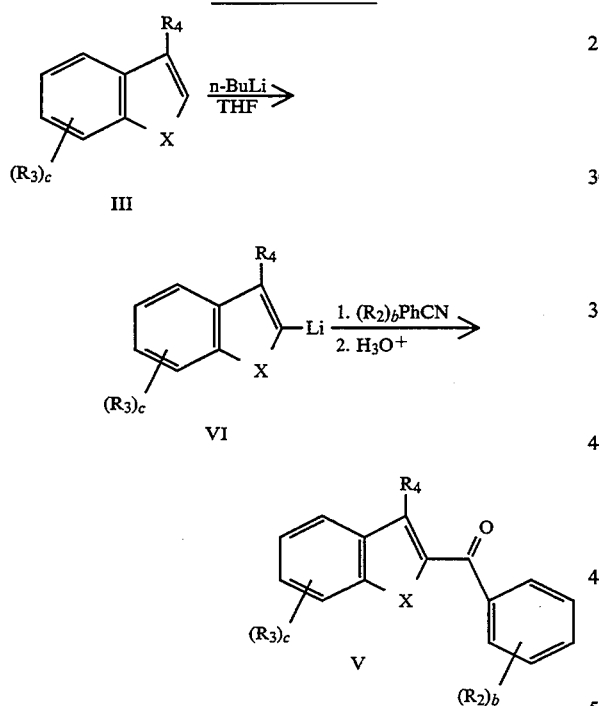

In Reaction B, the ketone represented by graphic formula V is reacted with sodium acetylide in a suitable solvent, such as anhydrous tetrahydrofuran, to form the corresponding propargyl alcohol represented by graphic formula VI.

REACTION B

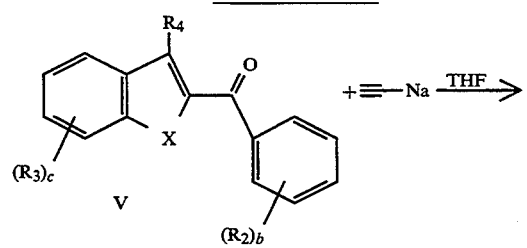

-continued
REACTION B

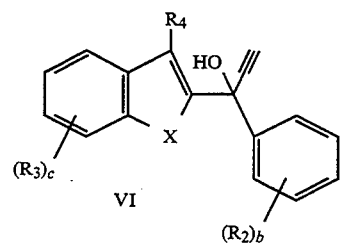

In Reaction C, the propargyl alcohol represented by graphic formula VI is coupled with a substituted or unsubstituted hydroxydibenzofuran, hydroxydibenzothiophene, or 2-naphthol represented by graphic formula VII, under acidic conditions to form the heterocyclic-fused benzopyran or benzo fused benzopyran of graphic formula I G. Other propargyl alcohols may be used in Reaction C to form compounds of graphic formula I having different substituents at the 2 position of the pyran ring.

REACTION C

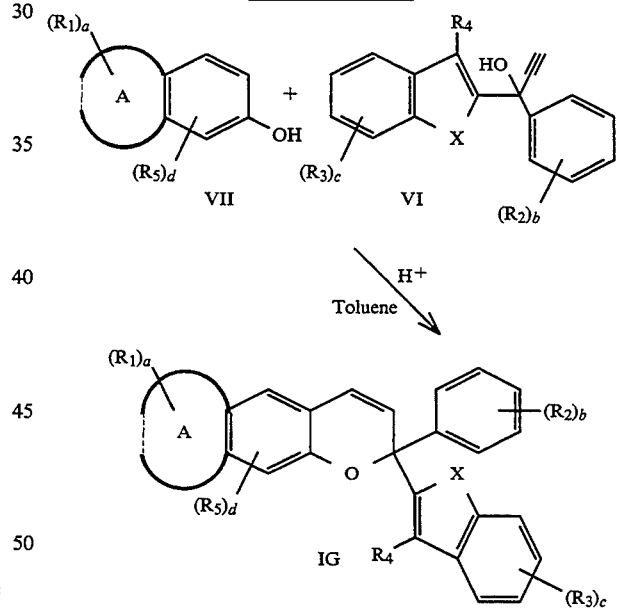

When either a 2-hydroxydibenzofuran or a 2-hydroxydibenzothiophene, represented by graphic formula VII A, is used in place of graphic formula VII in Reaction C, a minor amount, i.e., from about 5 to about 40 weight percent of the total product, of isomer represented by graphic formula I H may be produced in addition to a major amount, i.e., from about 60 to about 95 weight percent of the total product, of isomer represented by graphic formula I I as shown in Reaction D. A similar outcome would result for either a 3-hydroxydibenzofuran or a 3-hydroxydibenzothiophene used in place of graphic formula VII A in Reaction D.

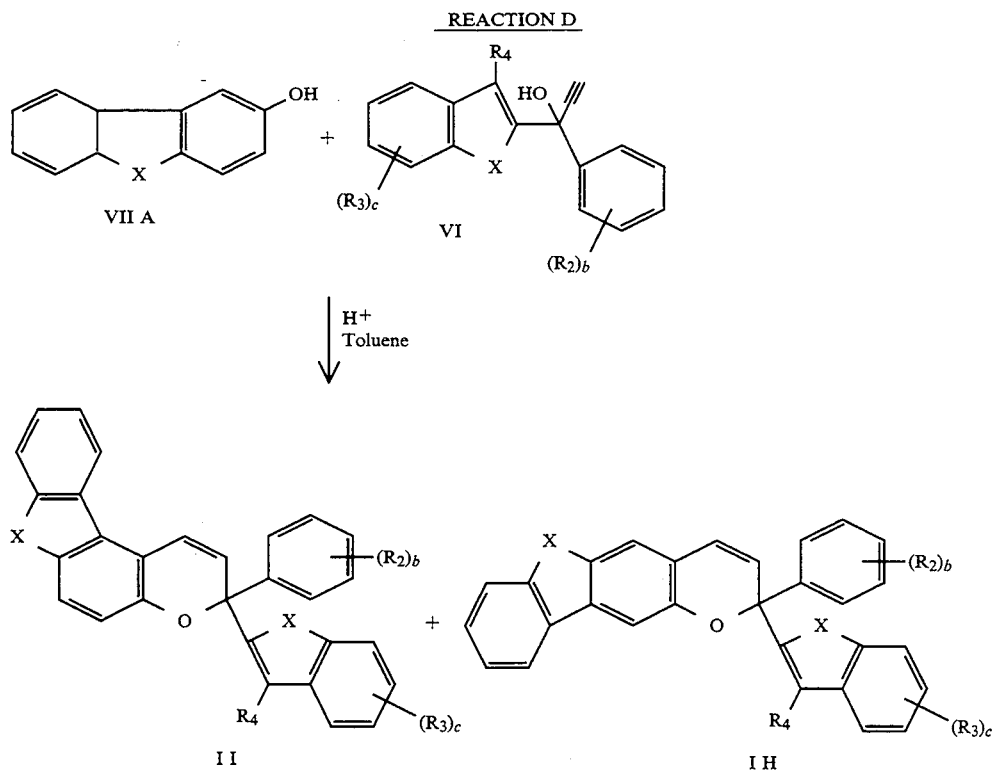

Hydroxydibenzofurans or hydroxydibenzothiophenes represented by the graphic formula VII B, when not commercially available, can be prepared by different pathways. As shown in Reaction E and described in further detail in the Journal of the American Chemical Society, Volume 61, 1939, page 951 and Volume 62, 1940, pages 667 to 669, treatment of compounds represented by graphic formula VIII with 2 equivalents of n-butyl lithium followed by reaction with an electrophile such as $CO_2$, $(CH_3)_2NCHO$, haloalkyl, cyanoalkyl, cyanophenyl, cyanonaphthyl, $CH_3ONH_2$, trialkoxyboride, halogen etc. ... will produce $R_5$ substituents such as —COOH, —CHO, alkyl, alkylcarbonyl, phenylcarbonyl, naphthylcarbonyl, —$NH_2$, —OH, halogen etc.

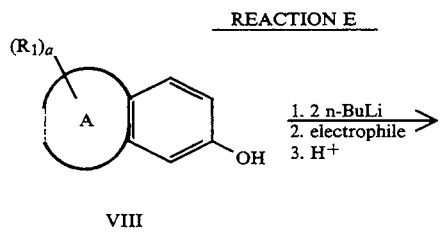

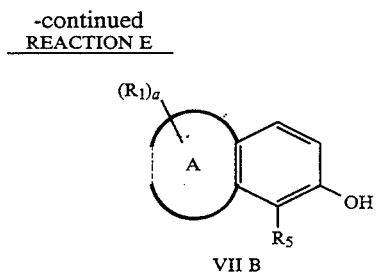

As shown in Reaction F, benzothiophenes or benzofurans having fused benzo substituents, represented by graphic formulae X and XI, may be prepared from substituted or unsubstituted 2,2' dihydroxybiphenyls represented by graphic formula IX. Compounds represented by graphic formulae X and XI may be used in place of VII in Reaction C to form heterocyclic fused benzopyrans of graphic formulae I C, I H, and I I. For further information on this reaction, see the Journal of the American Chemical Society, Volume 87(2), 1965, page 214.

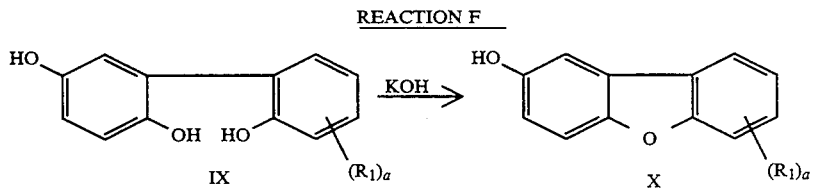

REACTION F -continued

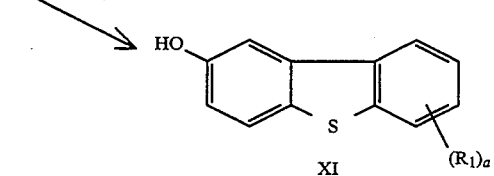

For further information, see *Heterocyclic Compounds*, Robert C. Elderfield, 1951, Vol. 2, Chapter 3 (Dibenzofuran) and Chapter 5 (Dibenzothiophene); *The Chemistry of Heterocyclic Compounds*, H. D. Hartough and S. L. Meisel, 1954, Vol. 7, Chapter IV (Dibenzothiophene and its Derivatives); *Advantages in Heterocyclic Chemistry*, A. R. Katritzky and A. J. Boulton, 1974, Vol. 16, Chapter V (Recent Advances in the Chemistry of Dibenzothiophenes); B. Akermark, H. Erdtman and C. A. Wachtmeister, *Acta Chemica Scandinavica*, Vol. 13, 1959, pages 1855–1862; S. Gronowitz, M. Herslof, R. Svenson, G. Bondesson and O. Magnusson, *Acta Pharm. Suec.*, Vol. 15 1978, pages 337–360; and French Patent 816,719 issued Aug. 16, 1937. As described in these references, several different substituents may be attached to the compound of graphic formula VIII by using a combination of reactions.

Compounds represented by graphic formula I, which also includes graphic formulae I A thru I I, may be used in those applications in which organic photochromic substances may be employed, such as optical lenses, e.g., vision correcting ophthalmic and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports, and drivers' licenses for which authentication or verification of authenticity may be desired. Benzopyrans represented by graphic formula I exhibit color changes from colorless to colors ranging from yellow to red/purple.

Examples of contemplated benzopyrans within the scope of the invention are the following:
  (a) 3-phenyl-3-(benzofur-2-yl)-3H-naphtho[2,1-b]pyran;
  (b) 3-(2-fluorophenyl)-3-(benzofur-2-yl)-3H-naphtho[2,1-b]pyran;
  (c) 3-phenyl-3-(benzothiophen-2-yl)-3H-naphtho[2,1-b]pyran;
  (d) 3-phenyl, 3-(benzofur-2-yl)-3H-benzo(b) furo[3,2-f]-1-benzopyran;
  (e) 3-phenyl-3-(benzothiophen-3-yl)-3H-naphtho[2,1-b]pyran;
  (f) 2-(2-methoxyphenyl)-2-(benzofur-2-yl)-2H-benzo (b) furo[2,3-g]-1-benzopyran;
  (g) 3-(2-fluorophenyl)-3-(benzofur-2-yl)-3H-benzo(b)thieno[3,2-f]-1-benzopyran;
  (h) 3-phenyl-3-(benzothiophen-2-yl)-3H-benzo (b)furo[3,2-f]-1-benzopyran;
  (i) 3-phenyl-3-(benzothiophen-3-yl)-3H-benzo(b)furo[3,2-f]-1-benzopyran; and
  (j) 3-(2-methoxyphenyl)-3-(benzofur-2-yl)-3H-benzo(b)thieno [3,2-f]-1-benzopyran.

Commercially available photoreactive inorganic glass lenses containing silver halide particles darken to a neutral gray or brown color in sunlight. In order to duplicate this color change in a plastic lens using the organic photochromic benzopyrans of graphic formula I, it is contemplated that such benzopyrans be used in combination with other appropriate complementary organic photochromic materials so that the desired gray or brown color shade is produced when the plastic lens containing such photochromic materials is exposed to ultraviolet light. For example, a compound which colors to yellow may be blended with a compound that colors to an appropriate purple to produce a brown shade. Similarly, a compound which is orange in its colored state will produce a shade of gray when used in conjunction with an appropriate blue coloring compound.

A first group of organic photochromic compounds contemplated for use as complementary photochromic materials are those having an activated absorption maximum within the visible range of greater than 590 nanometers, e.g., between about greater than 590 to about 700 nanometers. These materials typically exhibit a blue, blueish-green, or blueish-purple color when exposed to ultraviolet light in an appropriate solvent or matrix. Many of such compounds are described in the open literature. For example, spiro(indoline)naphthoxazines have been described, among others, in U.S. Pat. Nos. 3,562,172; 3,578,602; 4,215,010; and 4,342,668. Spiro(indoline)naphthoxazines having certain substituents on the 8' and 9' positions of the naphthoxazine portion of the molecule, such as 1,3,3-trimethyl-5-methoxy-9'-methoxycarbonyl-8'-acetoxy spiro[indoline-2,3'-[3H]naphth-[2,1b]-[1,4]oxazine, are the subject of co-pending U.S. patent application Ser. No. 07/993,587, filed Dec. 21, 1992. Spiro(indoline)pyridobenzoxazines are described in U.S. Pat. No. 4,637,698. Spiro(benzindoline)pyridobenzoxazines and spiro(benzindoline)naphthoxazines are described in U.S. Pat. No. 4,931,219. Spiro(benzindoline)naphthopyrans are described in Japanese Patent Publication 62/195383. Spiro(indoline)benzoxazines are described in U.S. Pat. No 4,816,584. Spiro(indoline)benzopyrans, spiro(indoline)naphthopyrans, and spiro(indoline)quinopyrans are described, for example, in U.S. Pat. No. 4,880,667. Benzopyrans and naphthopyrans having a nitrogen-containing substituent in the 2-position of the pyran ring are described in U.S. Pat. No. 4,818,096. Spiro(indoline)pyrans are also described in the text, *Techniques in Chemistry*, Volume III, "Photochromism," Chapter 3, Glenn H. Brown, Editor, John Wiley and Sons, Inc., New York, 1971.

A second group of organic photochromic substances contemplated for use as complementary photochromic compounds are those having at least one absorption maximum and preferably two absorption maxima, within the visible range of between about 400 and less than 550 nanometers. These materials typically exhibit a yellow to red/purple color when exposed to ultraviolet light in an appropriate solvent or matrix. Such compounds include certain chromenes, i.e., benzopyrans, 3H-naphtho[2,1-b]pyrans, and 2H-naphtho[1,2-b]pyrans many of which are described in the open literature, e.g., U.S. Pat. Nos. 3,567,605; 4,826,977; and 5,066,818. Examples of benzopyrans and naphthopyrans having a spiroadamantane group in the 2-position of the ring are described in U.S. Pat. No. 4,826,977. Naphthopyrans, i.e., 3H-naphtho[2,1-b]pyrans, having at least one ortho-substituted phenyl substituent at the 3-position of the pyran ring are described in U.S. Pat. No. 5,066,818. Naphthopyran compounds having certain substituents at the number 8 carbon atom and certain substituents at the number 7 or 9 carbon atom, all substituents being on the naphtho portion of the naphthopyran, are the subject of co-pending U.S. patent application Ser. No. 08/080,246, filed Jun. 21, 1993. Naphthopyrans substituted at the 3 position of the pyran ring with (i) an aryl substituent and (ii) a phenyl substituent having a 5- or 6-member heterocyclic ring fused at the number 3 and 4 carbon atoms of the phenyl substituent are the subject of co-pending U.S. patent application Ser. No.08/080,250 filed Jun. 21, 1993. Naphthopyran compounds substituted at the number 8 carbon atom on the naphtho portion of the naphthopyran ring, with for example, a methoxy group are the subject of U.S. Pat. No. 5,238,931. Naphthopyran compounds, examples of which are 3-aryl-3-arylalkenyl naphthophyrans, are the subject of co-pending U.S. patent application Ser. No. 07/954,630, filed Sep. 30, 1992. Naphthopyrans, i.e., 2H-naphtho[1,2-b]pyrans, having certain substituents at the number 5 and 6 carbon atoms of the naphtho portion of the naphthopyran and at the 2-position of the pyran ring are the subject of co-pending U.S. patent application Ser. No. 08/164,187, filed Dec. 9, 1993.

A third group of organic photochromic substances contemplated for use as complementary photochromic compounds are those having an absorption maximum within the visible range of between about 400 to about 500 nanometers and another absorption maximum within the visible range of between about 500 to about 700 nanometers. These materials typically exhibit color(s) ranging from yellow/brown to purple/gray when exposed to ultraviolet light in an appropriate solvent or matrix. Examples of these compounds include certain benzopyran compounds, such as those having substituents at the 2-position of the pyran ring and a substituted or unsubstituted heterocyclic ring, such as a benzothieno or benzofurano ring fused to the benz portion of the benzopyran. Such materials are the subject of co-pending U.S. patent application Ser. No. 08/030,932, filed Mar. 12, 1993.

The disclosures of such photochromic compounds in the aforedescribed patents and patent applications are incorporated herein, in toto, by reference. Photochromic articles containing a naphthopyran(s) of the present invention may contain also one of the aforesaid complementary photochromic compounds or a mixture of such photochromic compounds, as desired. Mixtures of photochromic compounds may be used to attain certain activated colors such as a near neutral gray or brown.

The novel benzopyran compounds of the present invention may be described as photochromic compounds that exhibit activated colors of from yellow to red/purple, and therefore may be used in place of or in combination with the aforesaid second group of photochromic compounds. The compounds of the present invention (hereinafter referred to as a second group photochromic compound) may be combined with or used in conjunction with the first group of photochromic compounds that color to purple/blue, e.g., the spirooxazine-type compounds, or with other photochromic substances in the aforesaid second group of photochromic compounds. Either members of the first or second group of photochromic compounds or mixtures of such compounds may be combined with or used in conjunction with the third group of described organic photochromic compounds that color from yellow/brown to purple/gray provided that the photochromic compounds of the third group are different than the photochromic compounds in the first and second groups. Each of the photochromic compounds or substances containing same described herein may be used in amounts and in a ratio such that an organic host material to which the mixture of compounds is applied or in which they are incorporated exhibits a desired resultant color, e.g., a substantially neutral color such as shades of gray or brown, when activated with unfiltered sunlight, i.e., as near a neutral color as possible given the colors of the activated photochromic compounds. The relative amounts of the aforesaid photochromic compounds used will vary and depend in part upon the relative intensities of the color of the activated species of such compounds, and the ultimate color desired. Generally, the weight ratio of the aforedescribed organic photochromic compound combinations, i.e., (first to second), (first to third), and (second to third), will vary from about 1:3 to about 3:1, e.g., between about 0.75:1 and about 2:1. The combination of the first, second, and third organic photochromic compounds may have a weight ratio that will vary from about 1:3:1 to 3:1:3.

A near neutral gray color exhibits a spectrum that has relatively equal absorption in the visible range between 400 and 700 nanometers, e.g., between 440 and 660 nanometers. A near neutral brown color exhibits a spectrum in which the absorption in the 440–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, N.Y. (1981). As used in the specification, a near neutral color is one in which the chromaticity coordinate values of "x" and "y" for the color are within the following ranges (D65 illuminant): $x=0.260$ to 0.400, $y=0.280$ to 0.400 following activation to 40 percent luminous transmission by exposure to solar radiation (Air Mass 1 or 2).

The photochromic compounds of the present invention may be applied to or incorporated into a host material by various methods described in the art. Such methods include dissolving or dispersing the compound within the host material, e.g., imbibition of the photochromic compound into the host material by immersion of the host material in a hot solution of the photochromic compound or by thermal transfer; providing the photochromic compound as a separate layer between adjacent layers of the host material, e.g., as a part of a polymeric film; and applying the photochromic compound as part of a coating placed on the surface of the host material. The term "imbibition" or "imbibe" is intended to mean and include permeation of the photochromic substance alone into the host material, solvent assisted transfer, absorption of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

The polymeric host material will usually be transparent, but may be translucent or even opaque. The polymeric product need only be transparent to that portion of the electromagnetic spectrum which activates the photochromic substance, i.e., that wavelength of ultraviolet (UV) light that produces the open form of the substance, and that portion of the visible spectrum that includes the absorption maximum wavelength of the substance in its UV activated form, i.e., the open form. Further, the resin color should not be such that it masks the color of the activated form of the photochromic substance, i.e., so the change in color is readily apparent to the observer. Preferably, the host material article is a solid transparent or optically clear material, e.g., materials suitable for optical applications, such as plano and vision correcting ophthalmic lenses, windows, automotive transparencies, e.g., windshields, aircraft transparencies, plastic sheeting, polymeric films, etc.

Examples of host materials which may be used with the photochromic substances or compositions described herein include: polymers, i.e., homopolymers and copolymers, of polyol(allyl carbonate) monomers, polymers, i.e., homopolymers and copolymers, of polyfunctional acrylate monomers, polyacrylates, poly(alkylacrylates) such as poly(methyl methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, polyesters, poly(ethylene terephthalate), polystyrene, copoly(styrene-methyl methacrylate), copoly(styrene-acrylonitrile), polyvinylbutyral, and polymers, i.e., homopolymers and copolymers, of diallylidene pentaerythritol, particularly copolymers with polyol (allyl carbonate) monomers, e.g., diethylene glycol bis(allyl carbonate) and acrylate monomers.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80-90 percent diethylene glycol bis(allyl carbonate) and 10-20 percent vinyl acetate, particularly 80-85 percent of the bis(allyl carbonate) and 15-20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups as described in U.S. Pat. No. 5,200,483; cellulose acetate, cellulose propionate, cellulose butyrate, cellulose acetate butyrate, polystyrene, and copolymers of styrene with methyl methacrylate, vinyl acetate, and acrylonitrile.

The amount of photochromic substance or composition containing same applied to or incorporated into a host material is not critical provided that a sufficient amount is used to produce a photochromic effect discernible to the human eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity. Generally, the amount of total photochromic substance incorporated into or applied to a photochromic optical host material may range from about 0.15 to about 0.35 milligrams per square centimeter of surface to which the photochromic substance(s) is incorporated or applied.

Adjuvant materials may also be incorporated into the host material with the photochromic substances prior to, simultaneously with or subsequent to application or incorporation of the photochromic substances in the host material. For example, ultraviolet light absorbers may be admixed with photochromic substances before their application to the host material or such absorbers may be superposed, e.g., superimposed, as a layer between the photochromic substance and the incident light. Further, stabilizers may be admixed with the photochromic substances prior to their application to the host material to improve the light fatigue resistance of the photochromic substances. Stabilizers, such as hindered amine light stabilizers and singlet oxygen quenchers, e.g., a nickel ion complex with an organic ligand, are contemplated. They may be used alone or in combination. Such stabilizers are described in U.S. Pat. No. 4,720,356. Finally, appropriate protective coating(s) may be applied to the surface of the host material. These may be abrasion resistant coatings and/or coatings that serve as oxygen barriers. Such coatings are known in the art.

The present invention is more particularly described in the following examples which are intended as illustrative only, since numerous modifications and variations therein will be apparent to those skilled in the art.

EXAMPLE 1

Step 1

2,3-Benzofuran (0.084 mole) was added to a reaction flask containing 100 milliliters of anhydrous tetrahydrofuran and stirred. The reaction was maintained under an argon atmosphere at −78° C. A 1.6 molar solution of n-butyl lithium in hexane (0.1 mole of n-butyl lithium) was added drop wise to the reaction which was stirred for 3 hours at −78° C. The cooling bath was removed and stirring was continued for 3 hours after the temperature of the reaction mixture reached room temperature. A solution of benzonitrile (0.084 mole, 8.7 grams in 20 milliliters of anhydrous tetrahydrofuran) was added dropwise and the reaction mixture was stirred for 16 hours at room temperature. A 5 weight percent aqueous hydrochloric acid solution (50 milliliters) was added to the reaction flask and the reaction mixture was refluxed for 5 hours. The reaction mixture was cooled to room temperature and the organic layer was separated. The aqueous layer was extracted with three 30 milliliter portions of diethyl ether. The extracts and organic layer were combined and washed with water. Benzoic acid that formed from the hydrolysis of unreacted benzonitrile was removed by washing the organic layer first with a 10 weight percent sodium hydroxide solution then with water. The washed organic layer was dried over anhydrous sodium sulfate. The solvents, diethyl ether, tetrahydrofuran, and hexane, were removed under vacuum to yield an oily product containing 2-benzoylbenzofuran, which was not purified but used directly in the next step.

Step 2

2-Benzoylbenzofuran, all of the material recovered from Step 1, was added to a reaction flask containing 100 milliliters of anhydrous tetrahydrofuran saturated with acetylene and stirred at room temperature under an argon atmosphere. An 18 weight percent suspension of sodium acetylide in xylene/mineral oil (a 10 percent molar excess of sodium acetylide) was added and the reaction mixture was stirred 16 hours at room temperature. The contents of the reaction flask was added to a 5 weight percent aqueous hydrochloric acid and ice mixture. The resulting mixture was extracted with diethyl ether. The organic layer was separated, washed, and dried over anhydrous sodium sulfate. The solvents were removed under vacuum to yield an oily product containing 1-phenyl-1-(benzofur-2-yl)-2-propyn-1-ol, which was not purified further but used directly in the next step.

Step 3

2-Naphthol (0.06 mole, 9.0 grams) and all of the 1-phenyl-1-(benzofur-2-yl)-2-propyn-1-ol from Step 2 were added to a reaction flask containing 200 milliliters of toluene and stirred at room temperature. A catalytic amount of p-toluenesulfonic acid (about 100 milligrams) was added and the mixture was stirred for about 6 hours. Afterwards, the reaction mixture was poured into water, the organic layer was separated and washed first with a 10 weight percent aqueous sodium hydroxide solution and then with water. The washed organic layer was dried over anhydrous sodium sulfate. The remaining toluene solvent was removed under vacuum. The resulting oil was purified using a silica gel column and a 1:3 mixture of chloroform:hexane as the eluant. The photochromic fractions were combined and the eluant was removed under vacuum. The resulting product was induced to crystallize from hexane. The recovered product, about 3.5 grams, had a melting point of 148° to 150° C. A nuclear magnetic resonance (NMR) spectrum showed the desired product to have a structure consistent with 3-phenyl-3-(benzofur-2-yl)-3H-naphtho[2,1-b]pyran.

EXAMPLE 2

The process of Example 1 was followed except that in Step 1, 2-fluorobenzonitrile (5.1 grams) was used in place of benzonitrile to produce 2-(2-fluorobenzoyl)-benzofuran; in Step 2, 2-(2-fluorobenzoyl)-benzofuran (8.0 grams, 0.033 mole) was used in place of 2-benzoylbenzofuran to produce 1-(2-fluorophenyl)-1-(benzofur-2-yl)-2-propyn-1-ol; and in Step 3, 1-phenyl-1-(2-fluorophenyl)-1-(benzofur-2-yl)-2-propyn-1-ol (4.5 grams) was used in place of 1-phenyl-1-(benzofur-2-yl)-2-propyn-1-ol. Product yield was 0.5 gram in the form of an oil. A nuclear magnetic resonance (NMR) spectrum showed the desired product to have a structure consistent with 3-(2-fluorophenyl)-3-(benzofur-2-yl)-3H-naphtho[2,1-b]pyran.

EXAMPLE 3

The process of Example 1 was followed except that in Step 1, benzo[b]thiophene (10.0 grams, 0.074 mole) was used in place of 2,3-benzofuran to produce 2-benzoylbenzothiophene; in Step 2, 2-benzoylbenzothiophene (6.0 grams, 0.025 mole) was used in place of 2-benzoylbenzofuran to produce 1-phenyl-1-(benzothiophen-2-yl)-2-propyn-1-ol; and in Step 3, 1.8 grams of 2-naphthol was used and 1-phenyl-1-(benzothiophen-2-yl)-2-propyn-1-ol (2.5 grams) was used in place of 1-phenyl-1-(benzofur-2-yl)-2-propyn-1-ol. The recovered product, 1.0 gram, had a melting point of 152° to 154° C. A nuclear magnetic resonance (NMR) spectrum showed the desired product to have a structure consistent with 3-phenyl-3-(benzothiophen-2-yl)-3H-naphtho[2,1-b]pyran.

EXAMPLE 4

The process of Example 1 was followed except that in Step 3, 2-hydroxydibenzofuran (2.0 grams) was used in place of 2-naphthol. Product yield was 1.5 grams in the form of an oil. A nuclear magnetic resonance (NMR) spectrum showed the product to have a structure consistent with 3-phenyl-3-(benzofur-2-yl)-3H-benzo(b)furo[3,2-f]-1-benzopyran as the major product, and 2-phenyl-2-(benzofur-2-yl)-2H-benzo(b)furo[2,3-g]-1-benzopyran, as the minor product. The product containing both major and minor isomers was used for further testing.

EXAMPLE 5

Step 1

Benzothiophene (0.037 mole) and benzoyl chloride (0.038 mole) were added to a reaction flask containing 50 milliliters of anhydrous methylene chloride and stirred at room temperature. Anhydrous aluminum chloride (0.04 mole) was added slowly to the mixture. The reaction mixture was stirred one hour and then poured into a 5 weight percent aqueous hydrochloric acid and ice mixture. The resulting mixture was stirred 15 minutes and extracted with methylene chloride. The organic layer was separated and washed first with 10 weight percent aqueous sodium hydroxide followed by distilled water. The organic layer was separated and dried over anhydrous magnesium sulfate. The methylene chloride solvent was removed under vacuum. The resulting oily product was a mixture of isomeric products. The 3-benzoyl derivative was the major product as determined by thin layer chromatography and was crystallized from hexane. The recovered product, 9 grams, was filtered and air dried. A nuclear magnetic resonance (NMR) spectrum showed the desired product to have a structure consistent with 3-benzoylbenzothiophene.

Step 2

The procedure of Step 2 of Example 1 was followed except that 3-benzoylbenzothiophene (9.0 grams) was used in place of 2-benzoylbenzofuran to produce 1-phenyl-1-(benzothiophen-3- yl)-2-propyn-1-ol.

Step 3

The procedure of Step 3 of Example 1 was followed except that 1-phenyl-1-(benzothiophen-3-yl)-2-propyn-1-ol (3.5 grams) was used in place of 1-phenyl-1-(benzofur-2-yl)-2-propyn-1-ol. The recovered product, 1.5 grams, had a melting point of 150° to 153° C. A nuclear magnetic resonance (NMR) spectrum showed the desired product to have a structure consistent with 3-phenyl-3-(benzothiophen-3-yl)-3H-naphtho[2,1-b]pyran.

EXAMPLE 6

The process of Example 1 was followed except that in Step 1, 2-methoxybenzonitrile (12.31 grams) was used in place of benzonitrile to produce 2-(2-methoxybenzoyl)-benzofuran; in Step 2, 2-(2-methoxybenzoyl)-benzofuran (10.0 grams, 0.039 mole) was used in place of 2-benzoylbenzofuran to produce 1-(2-methoxyphenyl)-1-(benzofur-2-yl)-2-propyn-1-ol; and in Step 3 2-hydroxydibenzofuran (4.0 grams, 0.021 mole) was used in place of 2-naphthol and 1-(2-methoxyphenyl)-1-(benzofur-2-yl)-2-propyn-1-ol (6.04 grams, 0.021 mole) was used in place of 1-phenyl-1-(benzofur-2-yl)-2-propyn-1-ol. The recovered crystalline product, 2.0 grams, had a melting point of 218° to 220° C. A nuclear magnetic resonance (NMR) spectrum showed the major product to have a structure consistent with 2-(2-methoxyphenyl)-2-(benzofur-2-yl)-2H-benzo(b)furo[2,3-g]-benzopyran. A minor amount of another isomeric product, 3-(2-methoxyphenyl)-3-(benzofur-2-yl)-3H-benzo(b)furo[3,2-f]-1-benzopyran, was observed in a thin layer chromatograph. The product containing the major isomer was used for further testing.

EXAMPLE 7

The procedure of Step 3 of Example 1 was followed except that 2-hydroxydibenzothiophene (1.0 gram) was used in place of 2-naphthol and 1-(2-fluorophenyl)-1-(benzofur-2-yl)-2-propyn-1-ol (4.0 gram) was used in place of 1-phenyl-1-(benzofur-2-yl)-2-propyn-1-ol. Product yield was 0.5 gram in the form of an oil. A nuclear magnetic resonance (NMR) spectrum showed the product to have a structure consistent with 3-(2-fluorophenyl)-3-(benzofur-2-yl)-3H-benzo(b)thieno[3,2-f]-1-benzopyran as the major product and 2-(fluorophenyl)-2-(benzofur-2-yl)-2H-benzo(b)thieno[2,3-g]-1-benzopyran as the minor product. The product containing both major and minor isomers was used for further testing.

EXAMPLE 8

The procedure of Step 3 of Example 1 was followed except that 2-hydroxydibenzofuran (2.3 grams, 0.0125 mole) was used in place of 2-naphthol and 1-phenyl-1-(benzothiophen-2-yl)-2-propyn-1-ol (2.5 grams) was used in place of 1-phenyl-1-(benzofur-2-yl)-2-propyn-1-ol. The recovered product, 1.0 gram, had a melting point of 158° to 160° C. A nuclear magnetic resonance (NMR) spectrum showed the major product to have a structure consistent with 3-phenyl-3-(benzothiophen-2-yl)-3H-benzo(b)furo[3,2-f]-1-benzopyran. A minor amount of another isomeric product, 2-phenyl-2-(benzothiophen-2-yl)-2H-benzo(b)furo[2,3-g]-1-benzopyran, was observed in a thin layer chromatograph. The product containing the major isomer was used for further testing.

EXAMPLE 9

The procedure of Step 3 of Example 1 was followed except that 2-hydroxydibenzofuran (4.0 grams) was used in place of 2-naphthol and 1-phenyl-1-(benzothiophen-3-yl)-2-propyn- 1-ol (4.5 grams) was used in place of 1-phenyl-1-(benzofur-2-yl)-2-propyn-1-ol. The recovered product, 0.8 gram, had a melting point of 175° to 178° C. A nuclear magnetic resonance (NMR) spectrum showed the product to have a structure consistent with 3-phenyl-3-(benzothiophen-3-yl)-3H-benzo(b)furo[3,2-f]-1-benzopyran as the major product and 2-phenyl-2-(benzothiophen-3-yl)-2H-benzo(b)furo[2,3-g]-1-benzopyran, as the minor product. The product containing both major and minor isomers was used for further testing.

EXAMPLE 10

The procedure of Step 3 of Example 1 was followed except that 2-hydroxydibenzothiophene (1.5 grams, 0.0075 mole) was used in place of 2-naphthol and 1-(2-methoxyphenyl)-1-(benzofur-2-yl)-2-propyn-1-ol (2.2 grams, 0.008 mole) was used in place of 1-phenyl-1-(benzofur-2-yl)-2-propyn-1-ol. The recovered product, 1.5 grams, had a melting point of 186° to 188° C. A nuclear magnetic resonance (NMR) spectrum showed the major product to have a structure consistent with 3-(2-methoxyphenyl)-3-(benzofur-2-yl)-3H-benzo(b)thieno[3,2-f]-1-benzopyran. A minor amount of another isomeric product, 2-(methoxyphenyl)-2-(benzofur-2-yl)-2H-benzo(b)thieno[2,3-g]-1-benzopyran, was observed in a thin layer chromatograph. The product containing the major isomer was used for further testing.

COMPARATIVE EXAMPLE 1

1,1-diphenyl-2-propyn-1-ol (20.8 grams, 0.1 mole) was added to a reaction flask containing 200 milliliters of benzene and 15 grams of 2-naphthol. The reaction mixture was warmed to 55° C. and after all of the 2-naphthol was dissolved, 0.25 gram of p-toluenesulfonic acid was added. The mixture changed from light tan to dark black in color and the temperature rose to 70° C. After a few minutes, the reaction mixture became lighter in color and began to cool. Thirty minutes later, the contents of the flask were poured into 100 milliliters of 10 percent aqueous sodium hydroxide and shaken. The organic phase was separated, washed once with 10 percent aqueous sodium hydroxide, and then washed with water. The benzene solvent was removed on a rotary evaporator and the resulting light tan solid residue was slurried with 100 milliliters of hexane and then filtered. The filtered solid was washed again with 100 milliliters of hexane and dried to provide 18.4 grams of the product, 3,3-diphenyl-3H-naphtho [2,1-b]pyran. The solid product had a melting point of 156°–158° C. and was 98 percent pure as determined by liquid chromatographic analysis.

COMPARATIVE EXAMPLE 2

The procedure of Step 3 of Example 1 was followed except that 2-hydroxydibenzofuran (1.3 grams) was used in place of 2-naphthol and 1,1-diphenyl-2-propyn-1-ol (1.5 grams) was used in place of 1-phenyl-1-(benzofur-2-yl)-2-propyn-1-ol. The recovered product, 1.0 gram, had a melting point of 137° to 140° C. A nuclear magnetic resonance (NMR) spectrum showed the major product to have a structure consistent with 3,3-diphenyl-(3H)-benzo(b)furo[3,2-f]-1-benzopyran. A minor amount of another isomeric product, 2,2-diphenyl-2H-benzo(b)furo[2,3-g]-1-benzopyran, was observed in a thin layer chromatograph. The product containing both major and minor isomers was used for further testing.

EXAMPLE 11

Part A

The photochromic compounds prepared in the Examples and the Comparative Examples were incorporated into an ethyl cellulose resin by the following procedure. About 30 milligrams of the photochromic compound was added to 2.0 grams of a 10 weight percent ethyl cellulose solution in toluene. The photochromic compound was dissolved by warming and stirring on a steam bath. Approximately 2.0 grams of the resultant solution was deposited on the edge of a 75 by 25 millimeter (mm) glass slide. Using a draw down bar, a 0.2 mm layer of photochromic resin solution was placed evenly on the slide and permitted to dry.

Part B

The photochromic test samples prepared in Part A were tested for photochromic response rates on an optical bench. Prior to testing on the optical bench, the photochromic test samples were exposed to 365 nanometer (nm) ultraviolet light for about 15 minutes to activate the photochromic compounds and then placed into a 76° C. oven for about 15 minutes to bleach or inactivate the photochromic compounds. The test samples were then cooled to room temperature, exposed to fluorescent room lighting for at least 2 hours and then kept covered for at least 2 hours prior to testing on an optical bench maintained at 75° F. (23.9° C.).

The optical bench comprises a 150 watt Xenon arc lamp, a tungsten lamp, power supplies for both lamps, condensing lenses as needed to maintain collimated light beams from both lamps, a remote controlled shutter, a copper sulfate bath acting as a heat sink for the arc lamp, a Schott WG-320 nm cut-off filter which removes short wavelength radiation, neutral density filter(s), a sample holder in which the sample to be tested is inserted, a photopic filter, light detector, and radiometer assembly, a strip chart recorder, and a means for maintaining the alignment of the aforestated components during testing.

Change in optical density ($\Delta$OD) of a sample was determined by inserting a photochromic test sample in the bleached state into the sample holder, adjusting the transmittance scale to 100%, opening the shutter from the Xenon lamp to provide ultraviolet radiation to change the sample from the bleached state to an activated (darkened) state, measuring the transmittance through the sample. The transmittance was measured by directing a beam of light from the tungsten lamp at a small angle normal to the surface of the sample, through the sample, and to a photopic filter, light detector and radiometer assembly. The photopic filter passes wavelengths such that the detector mimics the response of the human eye and produces output signals that are processed by the radiometer. The change in optical density was calculated according to the formula $\Delta OD = \log(100/\% Ta)$ where % Ta is the percent transmittance in the activated state and the logarithm is to the base 10.

The $\Delta$ OD/Min, which represents the sensitivity of the photochromic compound's response to UV light, was measured over the first five (5) seconds of UV exposure, then expressed on a per minute basis. The saturation optical density (OD) was taken under identical conditions as the $\Delta$ OD/Min, except UV exposure was continued for 15 minutes. The lambda max value, which is the maximum absorption of the activated (colored) form of the photochromic compound in ethyl cellulose resin, may occur at one or two wavelengths reported as Band A and Band B in Table 1. The Bleach Rate T ½ is the time interval in seconds for the absorbance of the activated form of the benzopyran in the test sample to reach one half the highest absorbance at room temperature (72° F., 22.2° C.) after removal of the source of activating light. Results are tabulated in Table 1.

TABLE 1

| | LAMBDA MAX | | SENSITIVITY | OD | BLEACH RATE |
|---|---|---|---|---|---|
| | BAND A | BAND B | $\Delta$ OD/MIN | @ SAT | T ½ (SEC.) |
| COMPOUND EXAMPLE | | | | | |
| 1 | 467 | — | 1.15 | 0.95 | 345 |
| 2 | 462 | — | 0.59 | 0.84 | >1800 |
| 3 | 460 | — | 0.76 | 0.52 | 122 |
| 4 | 453 | 482 | 0.26 | 0.34 | 311 |
| 5 | 440 | — | 0.62 | 0.34 | 93 |
| 6 | 448 | 507 | 0.49 | 0.86 | >1200 |
| 7 | 482 | — | 0.27 | 0.27 | 620 |
| 8 | 476 | 545 | 0.25 | 0.23 | 226 |
| 9 | 444 | 515 | 0.22 | 0.18 | 178 |
| 10 | 482 | 532 | 0.66 | 0.98 | >1200 |
| COMPARATIVE EXAMPLE | | | | | |
| 1 | 432 | — | 0.87 | 0.31 | 32 |
| 2 | 430 | 522 | 0.42 | 0.18 | 85 |

The results of Table 1 show that each of the tested compounds of the present invention have bleach rates and lambda max Band A values higher than the Comparative Examples. The Compound Examples exhibit a significant bathochromic shift in Band A versus the Comparative Examples, which results in the Compound Examples demonstrating a different activated color.

Regarding the OD at saturation, each of the tested compounds, except Compound Examples 7, 8, and 9, have values greater than Comparative Example 1 and all of the Compound Examples have values greater than Comparative Example 2. The sensitivity of Compound Example 1 is greater than Comparative Examples 1 and 2 and the Compound Examples 2, 3, 5, 6, and 10 have sensitivity values greater than Comparative Example 2.

The results of Table 1 for the tested compounds of the present invention demonstrate the effects of each compound having a different substituent on the parameters tested, such as, visible spectra, i.e., lambda max; fade rate, i.e., bleach rate; activated intensity, i.e., OD at saturation; and coloration rate, i.e., sensitivity.

The present invention has been described with reference to specific details of particular embodiments thereof, it is not intended that such details be regarded as limitations upon the scope of the invention except insofar as to the extent that they are included in the accompanying claims.

I claim:

1. A benzopyran compound represented by the following graphic formula:

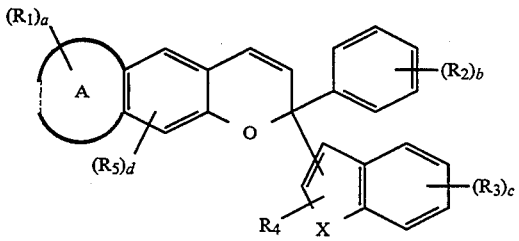

wherein (a) A is selected from the group consisting of benzothieno, benzofurano, and benzo, the 2,3 position of said benzothieno or benzofurano group being fused to the f, g, or h side of said benzopyran compound, said benzo group being fused to the f side of the benzopyran, and X is oxygen or sulfur;

(b) each $R_1$ is $C_1$-$C_5$ alkyl, $C_5$-$C_7$ cycloalkyl, $C_1$-$C_5$ alkyl substituted $C_5$-$C_7$ cycloalkyl, $C_1$-$C_5$ alkylcarbonyl, $C_1$-$C_5$ alkoxycarbonyl, halo($C_1$-$C_5$)alkylcarbonyl, $C_1$-$C_5$ monoalkylaminocarbonyl, formyl, halogen, R(R')N—, or the group —O—L, wherein R is a $C_1$-$C_3$ alkyl, R' is hydrogen or $C_1$-$C_3$ alkyl, L is hydrogen, $C_1$-$C_5$ alkyl, phenyl($C_1$-$C_3$)alkyl, $C_1$-$C_5$ alkylcarbonyl, halo($C_1$-$C_5$)alkylcarbonyl, $C_1$-$C_5$ monoalkylaminocarbonyl, acrylyl, methacrylyl, acetonyl, pyridyl, or substituted or unsubstituted arylcarbonyl, said aryl of the arylcarbonyl group being phenyl or naphthyl, said aryl substituents being $C_1$-$C_5$ alkyl, $C_1$-$C_5$ alkoxy, halogen, $C_5$-$C_7$ cycloalkyl, or $C_1$-$C_5$ alkyl substituted $C_5$-$C_7$ cycloalkyl; and (c) Each $R_2$ is $C_1$-$C_5$ alkyl, $C_5$-$C_7$ cycloalkyl, halogen, R(R')N—, or the group —O—L', wherein L' is hydrogen, $C_1$-$C_5$ alkyl, phenyl($C_1$-$C_3$)alkyl, acrylyl, or methacrylyl; each $R_3$ is $C_1$-$C_5$ alkyl or $C_1$-$C_5$ alkoxy; $R_4$ is hydrogen or $C_1$-$C_5$ alkyl; each $R_5$ is $C_1$-$C_5$ alkyl, $C_5$-$C_7$ cycloalkyl, $C_1$-$C_5$ alkylcarbonyl, $C_1$-$C_5$ alkoxycarbonyl, halo($C_1$-$C_5$)alkylcarbonyl, $C_1$-$C_5$ monoalkylaminocarbonyl, formyl, halogen, cyano, R(R')N—, or the group —O—L, wherein R, R' and L are as defined for $R_1$; said halogen (or halo) groups in $R_1$, $R_2$ and $R_5$ being chloro, fluoro, or bromo; and a, b, c, and d are each the integers 0, 1, or 2, provided that when A is benzo, a and d are each 0.

2. The benzopyran compound of claim 1 wherein:

(a) A is a benzo group or a benzothieno or benzofurano group represented by the following graphic formula:

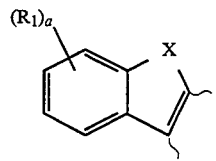

wherein X is oxygen or sulfur; each $R_1$ is a $C_1$-$C_3$ alkyl, $C_5$-$C_6$ cycloalkyl, $C_1$-$C_3$ alkylcarbonyl, $C_1$-$C_3$ alkoxycarbonyl, halo($C_1$-$C_2$)alkylcarbonyl, $C_1$-$C_3$ alkylaminocarbonyl, formyl, chloro fluoro, R(R')N—, or the group —O—L, wherein R is a $C_1$-$C_2$ alkyl, R' is hydrogen or $C_1$-$C_2$ alkyl, L is $C_1$-$C_3$ alkyl, phenyl($C_1$-$C_2$)alkyl, $C_1$-$C_3$ alkylcarbonyl, $C_1$-$C_3$ alkoxycarbonyl, halo($C_1$-$C_2$)alkylcarbonyl, $C_1$-$C_3$ monoalkylaminocarbonyl, acrylyl, or methacrylyl; and (b) each $R_2$ is $C_1$-$C_3$ alkyl, $C_5$-$C_6$ cycloalkyl, fluoro R(R')N—, or the group —O—L', wherein R is a $C_1$-$C_2$ alkyl, R' is hydrogen or $C_1$-$C_2$ alkyl, L' is $C_1$-$C_3$ alkyl, phenyl($C_1$-$C_2$)alkyl, acrylyl, or methacrylyl; each $R_3$ is $C_1$-$C_3$ alkyl or $C_1$-$C_3$ alkoxy; $R_4$ is hydrogen or $C_1$-$C_3$ alkyl; each $R_5$ is formyl, $C_1$-$C_3$ alkyl, $C_5$-$C_6$ cycloalkyl, $C_1$-$C_3$ alkylcarbonyl, $C_1$-$C_3$ alkoxycarbonyl, halo($C_1$-$C_3$)alkylcarbonyl, $C_1$-$C_3$ monoalkylaminocarbonyl, fluoro, R(R')N—, or the group —O—L, wherein R, R' and L are as defined for $R_1$; said halo group in $R_1$ and $R_5$ being chloro or fluoro; and a, b, c, and d are each the integers 0 or 1.

3. The benzopyran of claim 2 wherein each $R_1$ is formyl, methyl, methoxycarbonyl, methylaminocarbonyl, or methoxy; each $R_2$ is methyl, methoxy, or fluoro; each $R_3$ is methyl or methoxy; $R_4$ is a methyl; and each $R_5$ is a formyl, methyl, methoxycarbonyl, methylaminocarbonyl, or methoxy.

4. A benzopyran selected from the group consisting of:

(a) 3-phenyl-3-(benzofur-2-yl)-3H-naphtho[2,1-b]pyran;

(b) 3-(2-fluorophenyl)-3-(benzofur-2-yl)-3H-naphtho[2,1-b]pyran;

(c) 3-phenyl-3-(benzothiophen-2-yl)-3H-naphtho[2,1-b]pyran;

(d) 3-phenyl-3-(benzofur-2-yl) -3H-benzo (b)furo[3,2-f]-1-benzopyran;

(e) 3-phenyl-3-(benzothiophen-3-yl)-3H-naphtho[2,1-b]pyran;

(f) 2-(2-methoxyphenyl)-2-(benzofur-2-yl)-2H-benzo (b)furo[2,3-g]-1-benzopyran;

(g) 3-(2-fluorophenyl)-3-(benzofur-2-yl)-3H-benzo(b)thieno[3,2-f]-1-benzopyran;

(h) 3-phenyl-3-(benzothiophen-2-yl)-3H-benzo(b)furo[3,2-f]-1-benzopyran;

(i) 3-phenyl-3-(benzothiophen-3-yl)-3H-benzo(b)furo[3,2-f]-1-benzopyran; and (j) 3-(2-methoxyphenyl)-3-(benzofur-2-yl)-3H-benzo(b)thieno[3,2-f]-1-benzopyran.

5. A photochromic article comprising an organic host material and a photochromic amount of a photochromic benzopyran compound of claim 1.

6. The photochromic article of claim 5 wherein the organic host material is selected from the group consisting of polyacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonate, polyurethane, poly(ethylene terephthalate), polystyrene, copoly(styrene-methylmethacrylate), copoly(styrene-acrylonitrile), polyvinylbutyral, and polymers of members selected from the group consisting of polyol(allyl carbonate) monomers, polyfunctional acrylate monomers, and diallylidene pentaerythritol monomers.

7. The photochromic article of claim 6, wherein the benzopyran compound is selected from the photochromic benzopyrans of claim 2.

8. The photochromic article of claim 6, wherein the benzopyran compound is selected from the photochromic benzopyrans of claim 3.

9. The photochromic article of claim 8 wherein the organic host material is a solid transparent homopolymer or copolymer of diethylene glycol bis(allyl carbonate), thermoplastic polycarbonate, poly(methylmethacrylate), polyvinylbutyral, or a polyurethane.

10. The photochromic article of claim 9 wherein the photochromic benzopyran compound is present in an amount of from about 0.15 to 0.35 milligrams per square centimeter of organic host material surface to which the photochromic substance (s) is incorporated or applied.

11. The photochromic article of claim 10 wherein the article is a lens.

12. A photochromic article comprising, in combination, a solid transparent polymerized organic host material and a photochromic amount of
   (a) at least one organic photochromic compound having at least one activated absorption maxima within the visible range of between about 400 and 700 nanometers associated with said host material, and
   (b) at least one photochromic benzopyran compound of claim 1.

13. The photochromic article of claim 12 wherein the organic host material is selected from the group consisting of polyacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonate, polyurethane, poly(ethylene terephthalate), polystyrene, copoly(styrene-methylmethacrylate), copoly(styrene-acrylonitrile), polyvinylbutyral, and polymers of members selected from the group consisting of polyol(allyl carbonate) monomers, polyfunctional acrylate monomers, and diallylidene pentaerythritol monomers.

14. The photochromic article of claim 13 wherein the photochromic benzopyran compound (b) is selected from the naphthopyran compounds of claim 2.

15. The photochromic article of claim 14 wherein the organic host material is a solid transparent homopolymer or copolymer of diethylene glycol bis(allyl carbonate), thermoplastic polycarbonate, poly (methylmethacrylate), polyvinylbutyral, or a polyurethane.

16. The photochromic article of claim 15 wherein the organic photochromic compound (a) is selected from the group consisting of spiro(indoline)naphthoxazines, spiro(indoline)pyridobenzoxazines, spiro(benzindoline)-pyridobenzoxazines, spiro(benzindoline)naphthoxazines, spiro(benzindoline)naphthopyrans, spiro(indoline)benzoxazines, spiro (indoline) benzopyrans, spiro (indoline) naphthopyrans, spiro (indoline) quinopyrans, spiro (indoline)pyrans, 3H-naphtho[2,1-b]pyrans, 2H-naphtho[2,1-b]pyrans, and mixtures of such photochromic substances.

17. The photochromic article of claim 16 wherein each photochromic compound associated with the organic host material is present in an amount of from about 0.15 to 0.35 milligrams per square centimeter of organic host material surface to which the photochromic compound is incorporated or applied.

18. The photochromic article of claim 17 wherein the article is an ophthalmic lens.

19. A photochromic article comprising, in combination, a solid transparent polymerized organic host material and a photochromic amount of
   (a) at least one organic photochromic compound represented by the graphic formula:

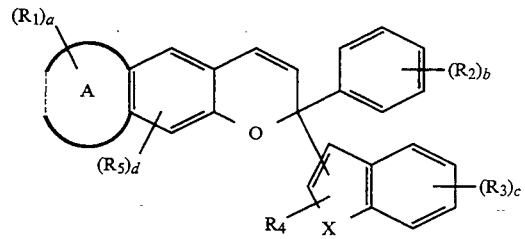

wherein, A is selected from the group consisting of benzothieno, benzofurano, and benzo, the 2,3 position of said benzothieno or benzofurano group being fused to the f, g, or h s side of said benzopyran compound, and said benzo group being fused to the f side of the benzopyran; X is oxygen or sulfur; each $R_1$ is $C_1$-$C_5$ alkyl, $C_1$-$C_5$ alkylcarbonyl, $C_1$-$C_5$ alkoxycarbonyl, $C_1$-$C_5$ monoalkylaminocarbonyl, formyl, or the group —O—L, wherein L is a $C_1$-$C_5$ alkyl; each $R_2$ is $C_1$-$C_5$ alkyl, fluoro, or the group —O—L', wherein L' is a $C_1$-$C_5$ alkyl; each $R_3$ is $C_1$-$C_5$ alkyl or $C_1$-$C_5$ alkoxy; $R_4$ is hydrogen or $C_1$-$C_5$ alkyl; each $R_5$ is formyl, $C_1$-$C_5$ alkyl, $C_1$-$C_5$ alkylcarbonyl, $C_1$-$C_5$ alkoxycarbonyl, $C_1$-$C_5$ monoalkylaminocarbonyl, or the group —O—L, wherein L is as defined for $R_1$; and a, b, c, and d are each the integers 0, 1, or 2, provided that when A is benzo, a and d are each 0;
   (b) at least one organic photochromic compound selected from the group consisting of spiro(indoline)naphthoxazines, spiro(indoline)pyridobenzoxazines, spiro(indoline)benzoxazines, spiro(indoline)benzopyrans, spiro(indoline)naphthopyrans, 2H-naphtho[2,1-b]pyrans, and 3H-naphtho[2,1-b]pyrans, the weight ratio of the photochromic compounds (a):(b) being from about 1:3 to about 3:1.

20. The photochromic article of claim 19 wherein the organic host material is a solid transparent homopolymer or copolymer of diethylene glycol bis(allyl carbonate), thermoplastic polycarbonate, poly(methylmethacrylate), polyvinylbutyral, or a polyurethane.

21. The photochromic article of claim 20 wherein each $R_1$ is methyl, methoxy, formyl, methoxycarbonyl, or methylaminocarbonyl; each $R_2$ is methyl, methoxy, or fluoro; each $R_3$ is methyl or methoxy; $R_4$ is methyl; and each $R_5$ is formyl, methyl, methoxycarbonyl, methylaminocarbonyl, or methoxy.

22. The photochromic article of claim 21 wherein the organic photochromic compound (b) is selected from spiro(indoline)naphthoxazines or spiro(indoline)pyrido benzoxazines.

* * * * *